United States Patent [19]

Schroeck

[11] 4,094,739
[45] June 13, 1978

[54] METHOD FOR PURIFYING MICROBIAL POLYSACCHARIDES

[75] Inventor: Calvin William Schroeck, Eastlake, Ohio

[73] Assignee: The Lubrizol Corporation, Wickliffe, Ohio

[21] Appl. No.: 754,866

[22] Filed: Dec. 27, 1976

[51] Int. Cl.² ............................................. C12D 13/04
[52] U.S. Cl. ....................................... 195/7; 195/31 P
[58] Field of Search .................... 195/31 P, 7, 4, 2, 11, 195/13, 111, 29

[56] References Cited
U.S. PATENT DOCUMENTS

| | | | |
|---|---|---|---|
| 3,436,346 | 4/1969 | Westover et al. | 195/31 P X |
| 3,591,578 | 7/1971 | Colin et al. | 195/31 P X |
| 3,994,780 | 11/1976 | Klass et al. | 195/13 |
| 4,010,071 | 3/1977 | Colegrove | 195/7 |

OTHER PUBLICATIONS

*The American Type Culture Collection Catalogue of Strains,* Rockville, Maryland, (1976), p. 310.

Laskin et al., *Handbook of Microbiology,* vol. 1, CRC Press, Cleveland, (1973), pp. 432, 767.

*Primary Examiner*—Raymond N. Jones
*Assistant Examiner*—Thomas G. Wiseman
*Attorney, Agent, or Firm*—James W. Adams, Jr.; William H. Pittman

[57] ABSTRACT

Microbial polysaccharides such as xanthan gum sometimes form cloudy suspensions rather than clear solutions when dispersed in water because of the presence of microbial cells therein. An aqueous polysaccharide solution (e.g., the fermentation broth) may be clarified by killing remaining microbial cells (e.g., by pasteurization) and conducting a second fermentation in the presence of an easily filterable microorganism capable of consuming said killed cells. The easily filterable microorganism is typically a fungus and preferably a mold such as the Trichoderma sp. molds. Following the second filtration, the cells of the easily filterable microorganism are preferably removed from the mixture, typically by filtration or centrifugation.

9 Claims, No Drawings

METHOD FOR PURIFYING MICROBIAL POLYSACCHARIDES

This invention relates to an improved method for clarifying and/or purifying products obtained by microbial fermentation. More particularly, it relates to a method for removing microbial cells from an aqueous mixture comprising a polysaccharide produced by microbial fermentation which comprises the steps of killing said microbial cells and causing said mixture to undergo a second fermentation in the presence of an easily separable microorganism capable of solubilizing said killed cells.

The microbial production of useful chemicals by fermentation of organic compounds (especially carbohydrates such as sugar and starch) in the presence of a suitable microorganism is a well known procedure. Typical products of such microbial fermentation (hereinafter sometimes called "microbial polysaccharides") are water-soluble gums useful in many applications including the preparation of foodstuffs and cosmetics and in secondary and tertiary oil recovery.

The microbial polysaccharide is normally obtained as an aqueous solution and may be recovered from said solution by conventional techniques such as precipitation or evaporation. As so recovered, however, it is frequently contaminated by insoluble cells of the microorganism used for fermentation. These cells are very difficult to separate from the microbial polysaccharide and their presence results in the formation of cloudy suspensions rather than clear solutions when the polysaccharide is dissolved in water. For many applications, the presence of insoluble impurities is undesirable. For example, such impurities tend to plug rock pores when an aqueous solution of the microbial polysaccharide is used for oil recovery by water-flooding. Filtration of the polysaccharide solution at the oil well site is frequently difficult and may be prohibitively expensive. Other methods for separating insolubles are also burdensome and costly.

A principal object of the present invention, therefor, is to provide a method for removing insoluble impurities, particularly microorganism cells, from microbial polysaccharides.

A further object is to provide a method for obtaining a microbial polysaccharide in a substantially completely water-soluble form, said method involving a minimum of processing steps.

Other objects will in part be obvious and will in part appear hereinafter.

Microbial polysaccharides and the methods for their production are well known, having been described in a large number of publications and patents. In general, they involve the cultivation of a suitable microorganism in an aqueous fermentation medium containing a carbohydrate. The microorganisms which are most likely to have cells so small as to be difficult or impossible to remove by filtration are the bacteria, of which many suitable varieties are disclosed in U.S. Pat. No. 3,406,114. Bacteria from the following list are illustrative of those suitable for this purpose; the especially suitable ones may be chosen from those marked with an asterisk.

*Alcaligenes faecalis* ATCC 212
*Arthrobacter viscosus* NRRL B-1973\*; B-1797
*Arthrobacter globiforme*\* NRCC
*Arthrobacter stabilis* NRRL B-3225
*Azotobacter indicum*\* (Beijerinckia indicum)
*Azotobacter vinelandii*
*Bacillus ethanicus*
*Bacillus polymyxa*
*Bacillus subtilis* NRCC 2035
*Bacterium aliphaticum liquefaciens*
*Bacterium hedium*
*Bacterium oligocarbophilus*
*Beggeotoa alba*
*Chromobacterium violaceum*
*Corynebacterium equi* subsp. *mucilaginosus* ATCC 21521
*Corynebacterium fascians*
*Corynebacterium fiaccumfaciens*\*
*Corynebacterium insidiosum* 110 Starr
*Corynebacterium michiganense*
*Corynebacterium rathayii*
*Corynebacterium sepedonicum*
*Corynebacterium tritici*
*Klebsiella aerogenes*
*Methanomonas methanica*
*Pseudomonas methanica*\*
*Rhizobium leguminosarum*
*Sphaerotilus natans*
*Streptomyces* sp.
*Thiotrix nivea*
*Xanthomonas campestris*\* NRRL B-1459
*Xanthomonas carotae* NRCC 10547
*Xanthomonas hederae*
*Xanthomonas hyacinthii* NRCC 12612
*Xanthomonas maculofoliigardeniae* NRCC 10201
*Xanthomonas malvaccarum* NRCC 12131
*Xanthomonas oryzae*
*Xanthomonas papavericola*
*Xanthomonas phaseoli* NRCC 11766
*Xanthomonas pruni*
*Xanthomonas stewartii*
*Xanthomonas translucens* NRCC 10772
*Xanthomonas vesicatoria*
*Xanthomonas vignicola* NRCC 11648
*Zoogloca ramigera*

Notable among the bacteria whose cells are too small to be conveniently removed from the polysaccharide by filtration or equivalent means are *Xanthomonas campestris*, especially *Xanthomonas campestris* NRRL B-1459. The polysaccharide product produced by the last-named bacterium is commonly known as "xanthan gum". Reference will frequently be made hereinafter to xanthan gum as the microbial polysaccharide being used, but it should be understood that the invention is applicable to any other suitable microbial polysaccharide and that other such polysaccharides are considered equivalent to xanthan gum for the purposes of this invention.

Xanthan gum and similar microbial polysaccharides are produced by a fermentation method well known to those skilled in the art. The immediate product of this method is a fermentation broth containing the polysaccharide, the microbe which has produced it, and other materials including various inorganic ions such as phosphate, nitrate, potassium and magnesium. The fermentation reaction is typically initiated by means of a seed culture which may contain an enzymatic protein material such as soy peptone. The pH of the fermentation broth is usually neutral or nearly so, typically 6.8–7.2.

The aqueous mixture which is the starting material in the method of this invention is ordinarily the fermentation broth. However, it is also within the scope of the invention to isolate xanthan gum from the broth and subsequently treat it by the method of this invention to remove microbial cells before use.

In the first step of the method of this invention, live microbial cells present in the aqueous mixture are killed. They may be killed by any suitable method, particularly acidification or "pasteurization" which comprises heating the mixture to at least about 60° C. and generally not more than about 100° C. Pasteurization is preferred.

In the second step, the aqueous mixture undergoes a second fermentation in the presence of an easily separable microorganism capable of solubilizing the killed cells of the microorganism previously used. As noted hereinabove, the cells of most bacterial microorganisms are so small that they cannot conveniently be removed by filtration, centrifugation or the like. The present invention is based on the discovery that other microorganisms having larger cell structure are more easily separable and will consume the killed cells of the microorganism previously used. In general, the easily separable microorganisms are fungi and may, for example, be selected from among those listed in the 1974 catalog of the American Type Culture Collection, pp. 153–247. The list on those catalog pages is incorporated by reference herein.

The preferred fungi are the molds and especially the Trichoderma sp. molds, including those identified as *Trichoderma viride*. Especially useful are Trichoderma sp. QM 6A and QM 9414.

Before the mold or other fungus is added for the second fermentation, it is frequently preferred to add to the fermentation broth or other aqueous solution a small amount of a carbohydrate such as glucose which may be consumed by the mold in preference to the product xanthan gum. If the bacterial cells have been killed by pasteurization, it is also frequently advantageous to acidify the broth (e.g., to a pH of about 3.0–5.0) so as to kill any bacterial cells which may have survived. While most bacteria cannot survive in acidic media, fungi can survive and propagate therein and it is feasible and often preferred to carry out the second fermentation reaction in an acidic solution.

Like the first fermentation, the second one is effected by adding a seed culture of the microorganism to the solution being fermented and agitating the same for a period of time adequate to solubilize the bacterial cells. The mechanism by which solubilization takes place is not critical for the purposes of this invention. It is probable that the mold either consumes the killed bacterial cells or denatures them by breaking them down into simpler molecules which are readily soluble in the aqueous system. In any event, the result is that the bacterial cells are no longer present, either alive or dead, in the xanthan gum solution.

Since the solubilization is effected by an easily separable microorganism, the latter may be removed from the aqueous system by conventional means including filtration, centrifugation and equivalents thereof. Removal is generally preferred and methods including a removal step are within the scope of the invention.

The clarity of xanthan gum solutions is inversely related to their turbidity, which is conveniently measured by determining their light absorbence. It has been found that the method of this invention reduces turbidity or light absorbence by amounts on the order of 95%, from which it will be apparent that said method is extremely effective for clarifying xanthan gum and similar microbial polysaccharides.

The method of this invention is illustrated by the following examples. All percentages are by weight unless otherwise indicated.

EXAMPLE 1

A flask is charged with sterile solutions comprising 9.7 grams of glucose, 0.43 gram of dipotassium hydrogen phosphate, 0.19 gram of ammonium nitrate, 0.043 gram of magnesium sulfate heptahydrate, 0.22 gram of soy peptone and water to provide a total reaction mixture weight of 430 grams. To this mixture is added 33 grams of a seed culture of *Xanthomonas campestris* NRRL B-1459, and the solution is shaken at 29° C. in the dark for about 67 hours. Periodic pH measurements are made and the pH is adjusted to about 6.8 by the addition of a sterile 10% aqueous solution of sodium hydroxide. After about 48 hours, an additional 200 ml. of sterile water is added.

The broth tests negative for glucose after about 67 hours. It is then pasteurized by heating for 1 minute in an autoclave at a setting of 100° C.; the estimated broth temperature is 70°–80° C. To the pasteurized solution is added 3 ml. of 1 M phosphoric acid, 5 ml. of a sterile 10% aqueous glucose solution and 100 ml. of sterile water. The solution is inoculated with 20 grams of a seed culture of Trichoderma sp. QM 6A and the mixture is shaken for an additional 25 hours and filtered using a cellulose filter aid. A clear solution is obtained. It is diluted to 2 liters and 0.6 gram of pentaethylene hexamine is added, followed by 1 M phosphoric acid to attain a pH of 3.5–4.0. The mixture is then diluted to 2400 ml. and centrifuged; the solid product (the amine salt of xanthan gum) is washed with dilute phosphoric acid, separated again by centrifugation and ground in a blender with 50 grams of dilute methanolic sodium hydroxide solution. The xanthan gum obtained thereby is filtered, washed with methanol and dried in vacuum.

EXAMPLE 2

The procedure of Example 1 is substantially repeated except that the mold used is Trichoderma sp. QM 9414. A similar clear aqueous solution is obtained from which xanthan gum is recovered as described in Example 1.

EXAMPLE 3

A solution is prepared by dissolving 6 grams of xanthan gum in 600 grams of sterile water. The mixture is pasteurized three times by heating for 1 minute at 100° C. (estimated mixture temperature of 70°–80° C. during pasteurization) at 24-hour intervals. It is then acidified with 1 M phosphoric acid to a pH of 3.8.

Two 100-gram portions of the pasteurized, acidified solution are prepared; to the first portion is added 1 gram of a sterile 10% glucose solution. Both portions are inoculated with a small amount of a seed culture of Trichoderma sp. QM 6A and shaken for 24 hours. Both are then filtered, yielding clear solutions with turbidities of 14 and 17 respectively, compared with 230 for a comparable aqueous solution of the starting xanthan gum.

EXAMPLE 4

A sterile fermentation system is constructed comprising a 5-gallon resin flask fitted with stirring means, condensing means, an air purge tube, a sampling tube, temperature measuring and regulating means, and means for measuring pH and supplying base (10% w/v aqueous sodium hydroxide) for pH adjustment. The flask is charged with 12 grams of a 0.1% solution of dipotassium hydrogen phosphate, 7.2 grams of a 0.06% solution of ammonium nitrate, 6 grams of a 0.05% solution of soy peptone, 1.2 grams of 0.01% solution of magnesium sulfate heptahydrate, 270 grams of a 2.25% solution of glucose, and enough water to provide a total volume of 12 liters. All of the solutions are sterile. The flask is maintained at about 29° C. and a seed culture of *Xanthomonas campestris* NRRL B-1459 (containing 18.5 grams of glucose) is added. The mixture is stirred and purged with air and the pH regulating system is adjusted so as to feed sodium hydroxide solution into the mixture to provide a pH of 6.9–7.1.

Fermentation is effected under the above-described conditions for about 88 hours after which the solution is pasteurized by heating to 80° C. and 6 liters of sterile water is added. By the addition of 1 M phosphoric acid, the pH is lowered to 4.4; the solution is then inoculated with a spore suspension of Trichoderma sp. QM 6A and a solution of 17.5 grams of glucose in 175 ml. of water. Fermentation is resumed and continued for about 26 hours, after which the mixture is filtered through filter cloth, diluted with 30 liters of distilled water and charged with 192 ml. of a 10% w/v aqueous solution of pentaethylene hexamine. A solution of 400 ml. of 1 M phosphoric acid in 2 liters of water is then added whereupon the xanthan gum amine salt precipitates. It is allowed to settle and the supernatant liquid is decanted; the solid amine salt is then centrifuged, washed with dilute phosphoric acid and methanol. The washed salt is contacted with methanolic sodium hydroxide and the freed xanthan gum is removed by filtration, washed with methanol and dried. The absorbence at 600 nm. of a 1% solution of the xanthan gum thus obtained is 0.052, as compared with 0.412 for a 0.2% solution of unclarified xanthan gum.

What is claimed is:

1. A method for removing bacterial cells from an aqueous mixture comprising a polysaccharide produced by bacterial fermentation which comprises the steps of killing said bacterial cells and causing said mixture to undergo a second fermentation with a Trichoderma sp. mold, said second fermentation being continued for a period of time adequate to effect solubilization of said killed cells.

2. A method according to claim 1 wherein the bacterial cells removed are *Xanthomonas campestris* cells.

3. A method according to claim 2 which includes the step of separating the mold cells from said mixture.

4. A method according to claim 3 wherein the mold cells are separated by filtration.

5. A method according to claim 4 wherein the aqueous mixture is the fermentation broth in which the polysaccharide was produced.

6. A method according to claim 5 wherein the bacterial cells are killed by heating said mixture to at least about 60° C.

7. A method according to claim 3 wherein the mold cells are separated by centrifugation.

8. A method according to claim 7 wherein the aqueous mixture is the fermentation broth in which the polysaccharide was produced.

9. A method according to claim 8 wherein the bacterial cells are killed by heating said mixture to at least about 60° C.

* * * * *